United States Patent
Balagurusamy et al.

(10) Patent No.: US 9,689,034 B2
(45) Date of Patent: *Jun. 27, 2017

(54) TARGETED SEQUENCING OF BIOMOLECULES BY PULLING THROUGH A LIQUID-LIQUID INTERFACE WITH AN ATOMIC FORCE MICROSCOPE

(71) Applicant: International Business Machines Corporation, Armonk, NY (US)

(72) Inventors: Venkat K. Balagurusamy, Suffern, NY (US); Stanislav Polonsky, Putnam Valley, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/602,860

(22) Filed: Jan. 22, 2015

(65) Prior Publication Data
US 2016/0053312 A1 Feb. 25, 2016

Related U.S. Application Data

(63) Continuation of application No. 13/915,430, filed on Jun. 11, 2013, now Pat. No. 8,978,161, which is a
(Continued)

(51) Int. Cl.
*C12Q 1/68* (2006.01)
*B82Y 35/00* (2011.01)
(Continued)

(52) U.S. Cl.
CPC ............ *C12Q 1/6869* (2013.01); *B82Y 35/00* (2013.01); *C12Q 1/68* (2013.01); *G01Q 60/24* (2013.01);
(Continued)

(58) Field of Classification Search
None
See application file for complete search history.

(56) References Cited

U.S. PATENT DOCUMENTS

| | | | |
|---|---|---|---|
| 5,420,805 | A | 5/1995 | Still et al. |
| 5,730,940 | A | 3/1998 | Nakagawa |

(Continued)

FOREIGN PATENT DOCUMENTS

| | | |
|---|---|---|
| CN | 1266283 A | 9/2000 |
| CN | 101614647 A | 12/2009 |
| JP | 10085000 A | 4/1998 |

OTHER PUBLICATIONS

Alexei Valiaev, Stefan Zauscher, and Scott C. Schmidler "Statistical Analysis of Single-Molecule AFM Force Spectroscopy Curves," Department of Statistical Science, Duke University, Durham, NC; 36 pages (Valiaev et al's work).

(Continued)

*Primary Examiner* — Betty Forman
(74) *Attorney, Agent, or Firm* — Cantor Colburn LLP; Vazken Alexanian

(57) ABSTRACT

A mechanism is provided for sequencing a biopolymer. The biopolymer is traversed from a first medium to a second medium. The biopolymer includes bases. As the biopolymer traverses from the first medium to the second medium, different forces are measured corresponding to each of the bases. The bases are distinguished from one another according to the different measured forces which are measured for each of the bases.

9 Claims, 17 Drawing Sheets

Related U.S. Application Data continuation of application No. 13/899,728, filed on May 22, 2013, now Pat. No. 8,950,011.

(51) Int. Cl.
  *G01Q 90/00* (2010.01)
  *G01Q 80/00* (2010.01)
  *G01Q 60/42* (2010.01)
  *G01Q 60/24* (2010.01)

(52) U.S. Cl.
  CPC .............. *G01Q 60/42* (2013.01); *G01Q 80/00* (2013.01); *G01Q 90/00* (2013.01); *C12Q 2565/601* (2013.01)

(56) References Cited

U.S. PATENT DOCUMENTS

| | | | | |
|---|---|---|---|---|
| 5,795,782 | A * | 8/1998 | Church | C07K 14/705 435/4 |
| 6,280,939 | B1 | 8/2001 | Allen | |
| 6,905,586 | B2 | 6/2005 | Lee et al. | |
| 7,745,129 | B1 * | 6/2010 | Schatz | C12Q 1/6874 435/6.1 |
| 8,132,268 | B2 | 3/2012 | Hugel et al. | |
| 2003/0033129 | A1 | 2/2003 | Spassov et al. | |
| 2004/0026618 | A1 | 2/2004 | Nakamura | |
| 2005/0009004 | A1 * | 1/2005 | Xu | G01N 33/48728 435/4 |
| 2005/0208554 | A1 | 9/2005 | Chan et al. | |
| 2006/0019247 | A1 * | 1/2006 | Su | C12Q 1/6869 435/6.17 |
| 2006/0060778 | A1 | 3/2006 | Fujihira et al. | |
| 2008/0286878 | A1 * | 11/2008 | Vezenov | B82Y 35/00 436/94 |
| 2010/0011472 | A1 | 1/2010 | Hugel et al. | |
| 2010/0048427 | A1 | 2/2010 | Mirkin et al. | |
| 2011/0124528 | A1 | 5/2011 | Luo et al. | |
| 2014/0034517 | A1 | 2/2014 | Akeson et al. | |

OTHER PUBLICATIONS

C. Bustamante, Z. Bryant, and S. Smith, "Ten Years of Tension: Single-Molecule DNA Mechanics," Department of Molecular and Cell Biology, and Department of Physics and Howard Hughes Medical Institute, University of CA, Berkeley, Nature, vol. 421, Jan. 23, 2003, www.nature.com/nature, 2003 Nature Publishing Group; 5 pages.

C. Ortiz and G. Hadziioannou, "Entropic Elasticity of Single Polymer Chains of Poly (methacrylic acid) Measured by Atomic Force Microscopy," 1999 American Chemical Society, Department of Polymer Chemistry, University of Groningen, Nijenborgh 4, Received Aug. 6, 1998; Revised Manuscript Nov. 30, 1998, Macromolecules 1999, 32, 780-787.

F. Ritort "Single-molecule Experiments in Biological Physics: Methods and Applications," Institute of Physics Publishing, Journal of Physics: Condensed Matter 18 (2006) R531-R583; Published Jul. 24, 2006 (Valiaev et al's work).

J. Albrecht, et al., "Free-Solutiuon Electrophoretic Separations of DNA-Drag-Tag Conjugates on Glass Microchips with No Polymer Network and No Loss of Resolution at Increased Electric Field Strength," Electrophoresis 2011, 32; pp. 1201-1208.

J. Paturej, et al., "Force Spectroscopy of Polymer Desorption: Theory and Molecular Dynamics Simulations," Soft Matter, 2014, 10; pp. 2785-2799.

K. Feldman, et al., "Toward a Force Spectroscopy of Polymer Surfaces," Langmuir 1998, 14, pp: 372-378.

Keir C. Neuman and Attila Nagy "Single-Molecule Force Spectroscopy: Optical Tweezers, Magnetic Tweezers and Atomic Force Microscopy," NIH Public Access, Nat Methods, Jun. 2008; 31 pages (Valiaev et al's work).

Keir C. Neuman and Steven M. Block, "Optical Trapping," Review of Scienfific Instruments, vol. 75, No. 9, Sep. 2004; 23 pages (Valiaev et al's work).

Matthias Rief et al., "Single Molecule Force Spectroscopy on Polysaccharides by Atomic Force Microscopy," Science 275, 1295 (1997); www.sciencemag.org, 4 pages (Valiaev et al's work).

R. Haynes, et al., "Comblike, Monodisperse Polypeptoid Drag-Tags for DNA Separations by End-Labeled Free-Solution Electrophoresis (ELFSE)," Bioconjugate Chem. 2005, 16; pp. 929-938.

S. Yamamoto, et al., "Atomic Force Microscopic Study of Stretching a Single Polymer Chain in a Polymer Brush," Macromolecules 2000, 33, pp. 5995-5998.

X.Zhang, C.Liu and W.Shi, "Force Spectroscopy of Polymers: Beyond Single Chain Mechanics," Physical properties of polymers handbook, Chapter 30, edited by J.E.Mark, 2007, Springer; 11 pages.

Y.-S., Lo, "Loading-Rate Dependence of Individual Ligand-Receptor Bond-Rupture Forces Studied by Atomic Force Microscopy," Langmuir 2001, 17; pp. 3741-3748.

* cited by examiner

The width of the dips or peaks in the saw-tooth structure provides direct measurement of the nanoscale length distribution of one block in the diblock polymer. Therefore the nanoscale composition of the diblock copolymer can be obtained from this saw-tooth shaped force-extension curve. 406

Depending on the nature of the solvent-polymer segment interaction, the first plateau region also might exhibit a saw-tooth shaped profile. 408

Initially AFM tip is brought closer to the bottom surface to attach to the free end of the DNA or RNA molecule. 601

Pull the AFM tip up to unwind and stretch the molecule, measuring the pulling force required simultaneously. 602

As the DNA or RNA molecule stretches from the random-coil or globular conformation in the solution, the measured force will show a plateau region in the force vs extension curve (Plateau-I). 603

Once the DNA or RNA molecule is pulled sufficiently long to cross the good solvent-bad solvent boundary in the top of the sample chamber, there will be an additional force on the AFM tip. This will exhibit a second plateau in the force – extension curve as the rest of the molecule crosses this boundary (Plateau-II). 604

The difference between the average force in the first and second plateau regions gives the differential force needed to cross the solvophillic (bottom) to solvophobic medium. This gives the solvophobic force. 605

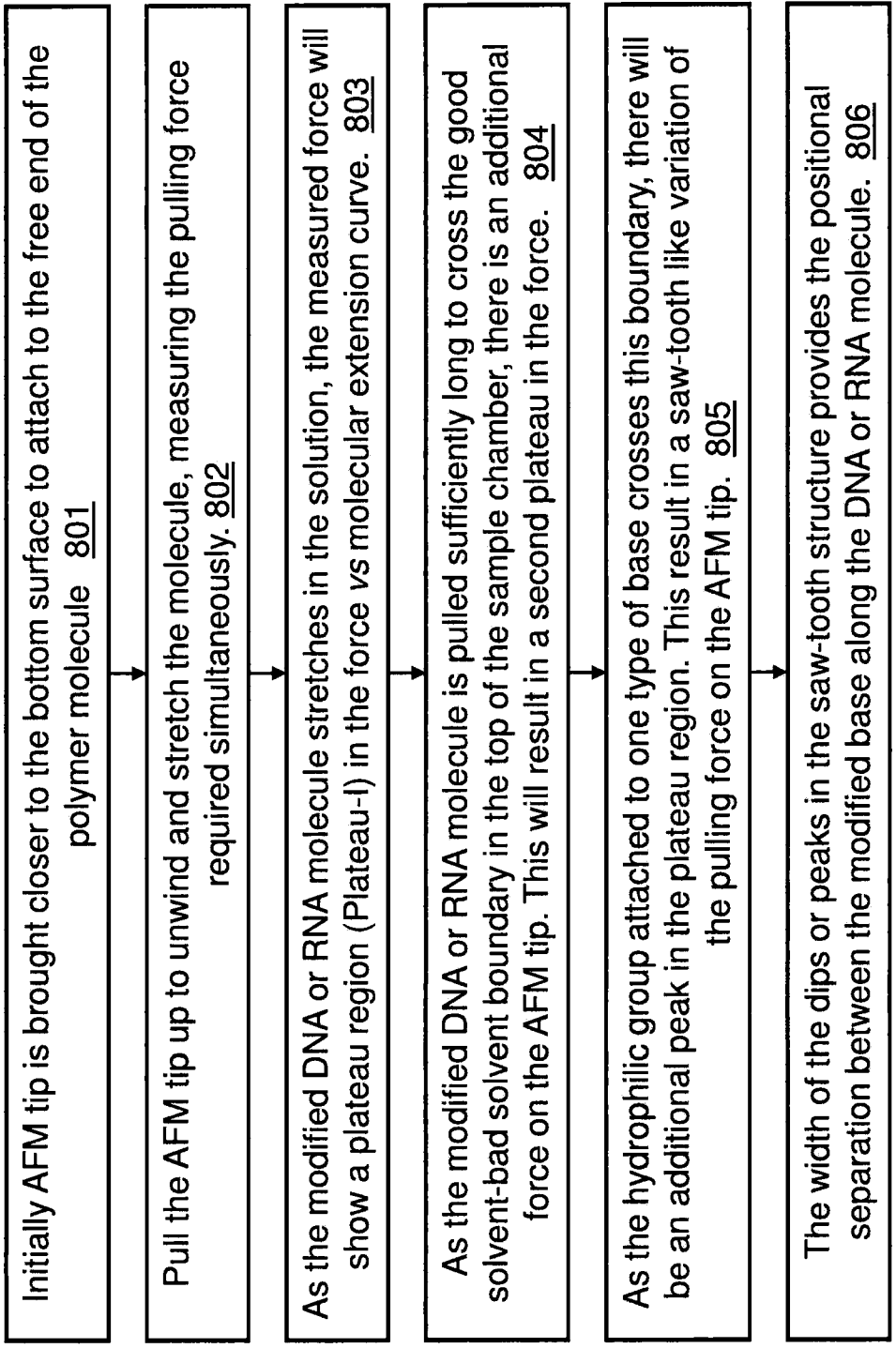

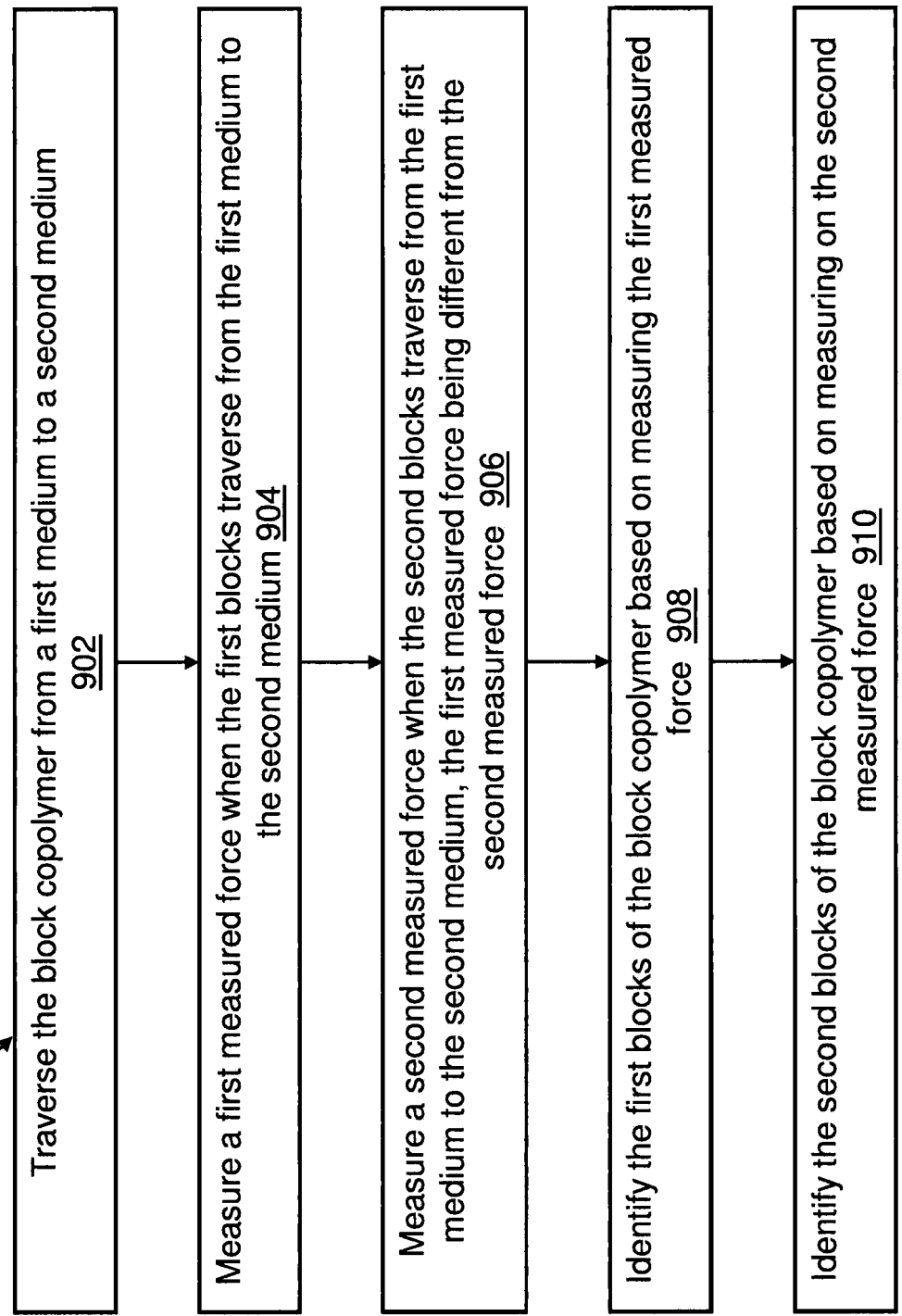

TARGETED SEQUENCING OF BIOMOLECULES BY PULLING THROUGH A LIQUID-LIQUID INTERFACE WITH AN ATOMIC FORCE MICROSCOPE

DOMESTIC PRIORITY

This application is a continuation of U.S. Non-Provisional application Ser. No. 13/915,430, entitled "TARGETED SEQUENCING OF BIOMOLECULES BY PULLING THROUGH A LIQUID-LIQUID INTERFACE WITH AN ATOMIC FORCE MICROSCOPE", filed Jun. 11, 2013 which is a continuation of U.S. Non-Provisional application Ser. No. 13/899,728, entitled "TARGETED SEQUENCING OF BIOMOLECULES BY PULLING THROUGH A LIQUID-LIQUID INTERFACE WITH AN ATOMIC FORCE MICROSCOPE", filed May 22, 2013, both of which are incorporated herein by reference in their entirety.

BACKGROUND

The present invention relates to sequencing, and more specifically to sequencing by pulling molecules (at a constant rate) through one medium to another medium.

Recently, there has been growing interest in applying nanopores as sensors for rapid analysis of biomolecules such as Deoxyribonucleic acid (DNA), Ribonucleic acid (RNA), proteins, etc. Special emphasis has been given to applications of nanopores for DNA sequencing, as the technology with the potential to reduce the cost of sequencing below $1000 per human genome.

Nanopore sequencing is a method for determining the order in which nucleotides occur on a strand of DNA. A nanopore is simply a small hole of the order of several nanometers in internal diameter. The theory behind nanopore sequencing has to do with what occurs when the nanopore is immersed in a conducting fluid and an electric potential (voltage) is applied across it: under these conditions a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be put around the nanopore so that DNA bases can be differentiated while the DNA passes through the nanopore.

SUMMARY

According to an embodiment, a method of sequencing a block copolymer is provided. The method includes traversing the block copolymer from a first medium to a second medium. The block copolymer comprises first blocks and second blocks. The method includes measuring a first measured force when the first blocks traverse from the first medium to the second medium, and measuring a second measured force when the second blocks traverse from the first medium to the second medium, where the first measured force is different from the second measured force. The method includes identifying the first blocks of the block copolymer based on measuring the first level of force and identifying the second blocks of the block copolymer based on measuring the second level of force.

According to an embodiment, a method of sequencing a biopolymer is provided. The method includes traversing the biopolymer from a first medium to a second medium, where the biopolymer includes bases. The method includes measuring different force levels corresponding to each of the bases as the biopolymer traverses from the first medium to the second medium and distinguishing the bases from one another according to the different measured forces measured for each of the bases.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 4A and 4B together illustrate a method for measuring the solvophobic energy and force of the diblock copolymer molecule in the bad solvent to good solvent medium boundary according to the second embodiment.

FIG. 6 illustrates a method for measuring the hydration and solvophobic force of the biomolecule according to the third embodiment.

FIG. 8 illustrates a method to obtain the position of the modified DNA bases attached to the large hydrophilic molecule according to the fourth embodiment.

FIG. 9 is a method of sequencing a block copolymer according to an embodiment.

DETAILED DESCRIPTION

Figure 1A:
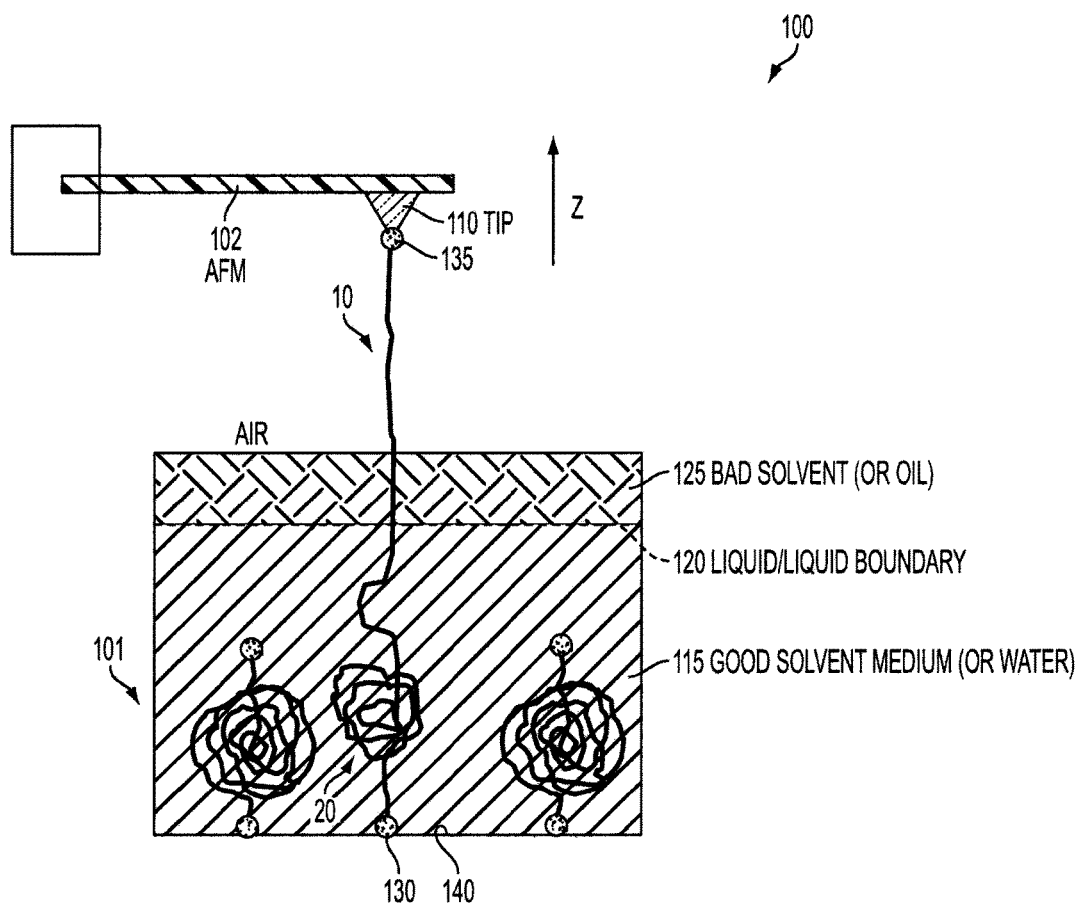
FIG. 1A illustrates an example setup for measuring the hydration and solvophobic force of a polymer strand according to a first embodiment.

Embodiments of the present invention relate to the field of DNA and RNA sequencing. There is much interest in obtaining the sequence information of the DNA or RNA molecule with single-molecule based techniques either by optical or electrical detection. Examples of these methods include nucleic acid base identification by synthesis and nanopore sequencing. Although various illustrations are provided for DNA and RNA, embodiments can also be utilized to determine the structural elements of proteins and sequence them.

The DNA molecule either double-stranded or single-stranded assumes a coil-like shape in solution such as, e.g., water due to its polymeric nature. The mechanical properties of a single DNA molecule have been widely studied using optical tweezers technique (C. Bustamante, "Ten years of tension: single-molecule DNA mechanics", Nature 421, 423-427 (2003); K. C. Neuman and S. M. Block, Review of Scientific Instruments 75, 2787 (2004)). Each of the two ends of a DNA molecule is attached to a special polymeric bead one of which will be trapped in the optical tweezers potential well and the other end held by the tip of a glass micropipette by suction (C. Bustamante et al op.cit.). When the DNA molecule is stretched it will look like a dumb-bell shape. As the glass micropipette is pulled away from the optical tweezers slowly with a feed-back controlled nanopositioner, the force being applied on the DNA can be measured from the displacement of the bead in the optical trap from its center with less than 0.1 picoNewton accuracy. These studies show that it requires only about 0.1 pico N (10-12 Newtons) to unwind the DNA from its coil conformation up to a length of ~0.65 of its contour length (Lc) and only <5 pN to stretch it to ~0.85Lc. On applying a force of ~65 pN the ds-DNA can be stretched to its full contour length. Continuous application of this amount of force makes the DNA undergo the overstretching transition.

Atomic force microscope (AFM) is a widely used technique to measure very small amount of forces (10-10 to 10-9 Newtons) acting between a surface and a sharp tip at the end of a cantilever (further discussed in the following which is herein incorporated by reference: K. C. Neuman and A. Nagy, Nature methods 5, 491 (2008); F. Ritort, Journal of Physics: Condensed Matter, 18, R531 (2006)). The force variation as the tip is scanned over the surface with a nanopositioner can be used to obtain surface topography and therefore also small molecules bound to the surface either physically or chemically. By either exploiting the physical adsorption of the molecules to the surface or their chemical attachment to the surface groups, one end of the molecule is held to the surface and the other by the AFM tip. A number of studies have been made ranging from protein folding/unfolding, biomolecular mechanics, their interactions with the surface, bond strengths of certain biomolecular interactions, polymer mechanics, and so forth ("Force Spectroscopy of Polymers: Beyond Single Chain Mechanics" by X. Zhang, C. Liu and W. Shi in Physical properties of polymers handbook, Chapter 30, Edited by J. E. Mark, 2007, Springer; C. Ortiz and G. Hadziioannou, Macromolecules, 32, 780-787 (1999), "Entropic elasticity of single polymer chains of poly(methacrylic acid) measured by atomic-force microscopy"; "Single molecule force spectroscopy on polysaccharides by atomic force microscopy", M. Rief, F. Oesterhelt, B. Heymann and H. E. Gaub, Science, 275, 1295-1297(1997)).

A charged polymer (such as DNA, RNA, or a protein molecule) that is stretched can become trapped between the gap created in a medium, for example, an air gap in water. The driving force for this trapping is the solvation energy gained by the part of the molecule that is exposed to air.

When a point charge moves from a dielectric medium with high permittivity ($\in 1$) to a low permittivity medium ($\in 2 < \in 1$), the point charge gains the solvation energy (Born energy) given by:

$$\frac{w_{Born}}{kT} = \frac{q_0}{r}\left(\frac{1}{\varepsilon 2} - \frac{1}{\varepsilon 1}\right) \qquad \text{Equation 1}$$

where $q_0 = e_0^2/2\ kT = 282$ Å at room temperature, and $e_0$ is the value of the electronic charge.

When the point charge leaves the water-air boundary, the gain in solvation energy amounts to approximately 200 kT, where k is Boltzmann's constant and T is temperature. This is equivalent to applying a force of about 500 pN (1 pico Newton=10-12 Newton) on the point charge to cross the boundary. Therefore, if one monitors the force on a charged polymer molecule stretched across a water-air boundary, there will be variations in the force needed to move the molecule across this boundary depending on the solvation energy variation for different parts of the molecule. This variation in the force for a charged polymer or a polymer with different types of molecular building blocks as in a diblock copolymer can be used to obtain the information about the position of the different segments along the molecule as explained in detail in the embodiments. This force corresponds to the solvophobic force.

A block copolymer is a polymer consisting of multiple sequences, or blocks, of the same monomer alternating in series with different monomer blocks. The blocks are covalently bound to each other (such as AAABBBAAA fashion, where A and B are two different types of monomers). Block copolymers are classified based on the number of blocks they contain and how the blocks are arranged. For example, block copolymers with two blocks are called diblocks; those with three blocks are triblocks; and those with more than three are called multiblocks. The positional occurrence of the other blocks can be either in a regular predictable way or can be random as in AAABBBAAABBBAAABBB . . . or AABBBABBAAAAB . . . , respectively. The diblock copolymers in which the second block occurs at random positions is called a random diblock copolymer.

Now turning to the figures, FIG. 1A is an example setup 100 for measuring the hydration and solvophobic force of a polymer strand according to an embodiment. One end of the polymer molecule 10 is bound to the bottom surface of the chamber 101 and the other end is bound to the tip 110 of the atomic force microscope 102. The polymer strand 10 can be bound to the either the sample chamber surface or the AFM tip by physical adsorption or chemical attachment. The polymer strand end can be covalently linked to a gold surface that acts as the bottom of the chamber through a thiol-modified end group of the polymer. For example, a monofunctional thiol-modified poly-methacrylic acid (PMMA-SH) can be synthesized and has been used in AFM studies of their entropic elasticity (C. Ortiz and G. Hadziioannou, Macromolecules, 32, 780-787 (1999), "Entropic elasticity of single polymer chains of poly(methacrylic acid)

measured by atomic-force microscopy"). In another example of the force spectroscopy studies of Dextran polymer strands, one end of them was attached to a gold surface by epoxy-alkanethiols ("Single molecule force spectroscopy on polysaccharides by atomic force microscopy", M. Rief, F. Oesterhelt, B. Heymann and H. E. Gaub, Science, 275, 1295-1297 (1997)). The other end was attached with streptavidin through reaction with carboxymethyl group per glucose unit on average which then bound to the biotin coated $Si_3N_4$ AFM tip allowing single polymer strand force spectroscopy studies. Further information regarding the atomic force microscope is discussed below.

Figure 1B:
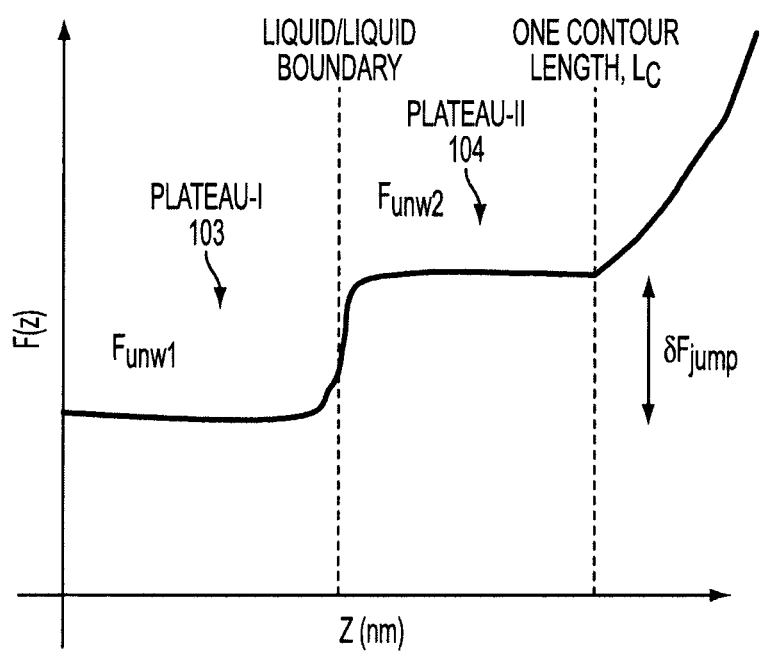
FIG. 1B illustrates a graph of the measured force versus molecular extension (F-x) curve according to the first embodiment.

Pulling (at a constant rate) the AFM tip 110 (upward in the Z direction) unwinds and stretches the molecule 10 as the tip 110 applies a force on the molecule 10, all while the whole molecule 10 is still in the good solvent medium 115. This force required to expose the segments of molecule 10 to the good solvent medium 115 as the molecule 10 unwinds from its random coil conformation 20 will result in a plateau (e.g., Plateau-I in FIG. 1A). FIG. 1B is a graph of the measured force versus molecular extension (F-x) curve according to the first embodiment in FIG. 1A. While unwinding the molecule 10 from its random coil conformation 20 (i.e., a ball) in the good solvent medium 115 by pulling the AFM tip 110 upward in the Z direction, the force (designated as force unwind 1 or Funw1) applied by the AFM tip 110 reaches the first plateau designated as Plateau-I for the section 103 of the curve.

Further pulling of the AFM tip 110 moves part of the molecule 10 to cross the good solvent medium 115 to a bad solvent medium boundary (i.e., liquid to liquid boundary 120) resulting in the second plateau (i.e., Plateau-II section 104) in the F-x curve. The force to cross the liquid to liquid boundary 120 and move the molecule through the bad solvent medium 125 is designated as force unwind 2 or Funw2. The difference between the average force in the two plateau regions (i.e., between Plateau-I and Plateau-II), δF=Funw1-Funw2, is the solvophobic force required to move the polymer molecule 10 from the good solvent medium 115 to the bad solvent medium 125. This solvophobic force is directly related to the solvophobic energy of the polymer (strand) molecule 10 in the bad solvent with respect to the good solvent. The polymer molecule 10 gains solvophobic energy in the bad solvent medium 125 compared to the good solvent medium 115. Solvation (also sometimes called dissolution), is the process of attraction and association of molecules of a solvent with molecules or ions of a solute. As ions dissolve in a solvent, they spread out and surround the solvent molecules.

Pulling the AFM tip 110 (upward in the Z direction) even further so that the extended molecule length is almost equal to its contour length Lc (contour length of a polymer is defined as the distance between two monomers x for the number of monomers that make up the polymer strand when the molecule 10 is in fully stretched conformation), the force will exhibit strong non-linear behavior which is related to the elastic property of the molecule 10 influenced by its chemical nature. When the AFM tip 110 extends the molecule 10 to its contour length Lc, there is a jump in the (measured) force needed to pull the molecule 10 in the z direction.

Figure 2:
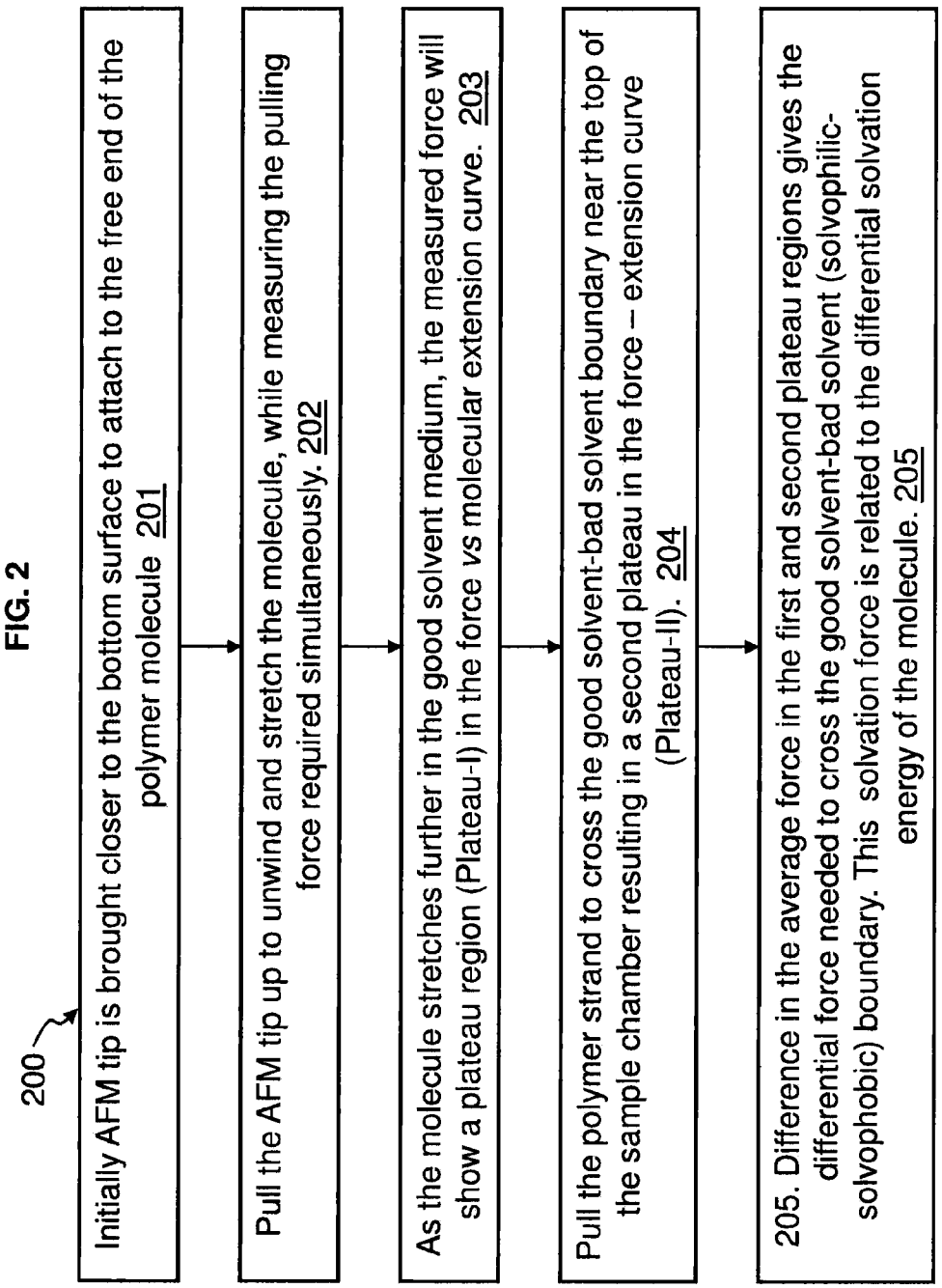
FIG. 2 illustrates a method for measuring the solvophobic force and solvophobic energy of the polymer molecule in the bad solvent to good solvent boundary according to the first embodiment.

According to the first embodiment, FIG. 2 illustrates a method 200 for measuring the solvophobic force and solvophobic energy of the polymer molecule 10 in the bad solvent medium 125 with respect to the good solvent medium illustrated in FIG. 1. The polymer molecule 10 is functionalized with special chemical groups to attach (130, FIG. 1) selectively to the bottom surface 140 of the sample chamber 101 and attach (135, FIG. 1) to the AFM tip 110. The AFM tip 110 is brought closer to the bottom surface 140 (of the chamber 101) to attach 135 to the free end of the polymer molecule 10 that will selectively bind to the AFM tip at block 201. The AFM tip 110 is pulled (at a constant rate) upward (away from the chamber 101) to unwind and stretch the molecule 10 while simultaneously measuring the force required to pull molecule 10 while still in the good solvent medium 115 at block 202. Stretching the molecule further (by pulling the AFM tip 110 upward further in the Z direction) in the good solvent medium 115 will exhibit a plateau region (Plateau-I) in the force-extension curve in FIG. 1B at block 203.

Now, pulling (at a constant rate) the polymer (strand) molecule 10 even further makes the segment of the molecule 10 cross the good solvent-bad solvent boundary 120 near the top of the sample chamber 101; this will result in a second plateau in the force-extension curve (Plateau-II) at block 204. At block 205, taking the difference in the average force in Plateau-I and Plateau-II regions is the solvophobic force directly related to the solvophobic energy of the polymer molecule 10 in the bad solvent medium 125 with respect to the good solvent medium 115.

Figure 3A:
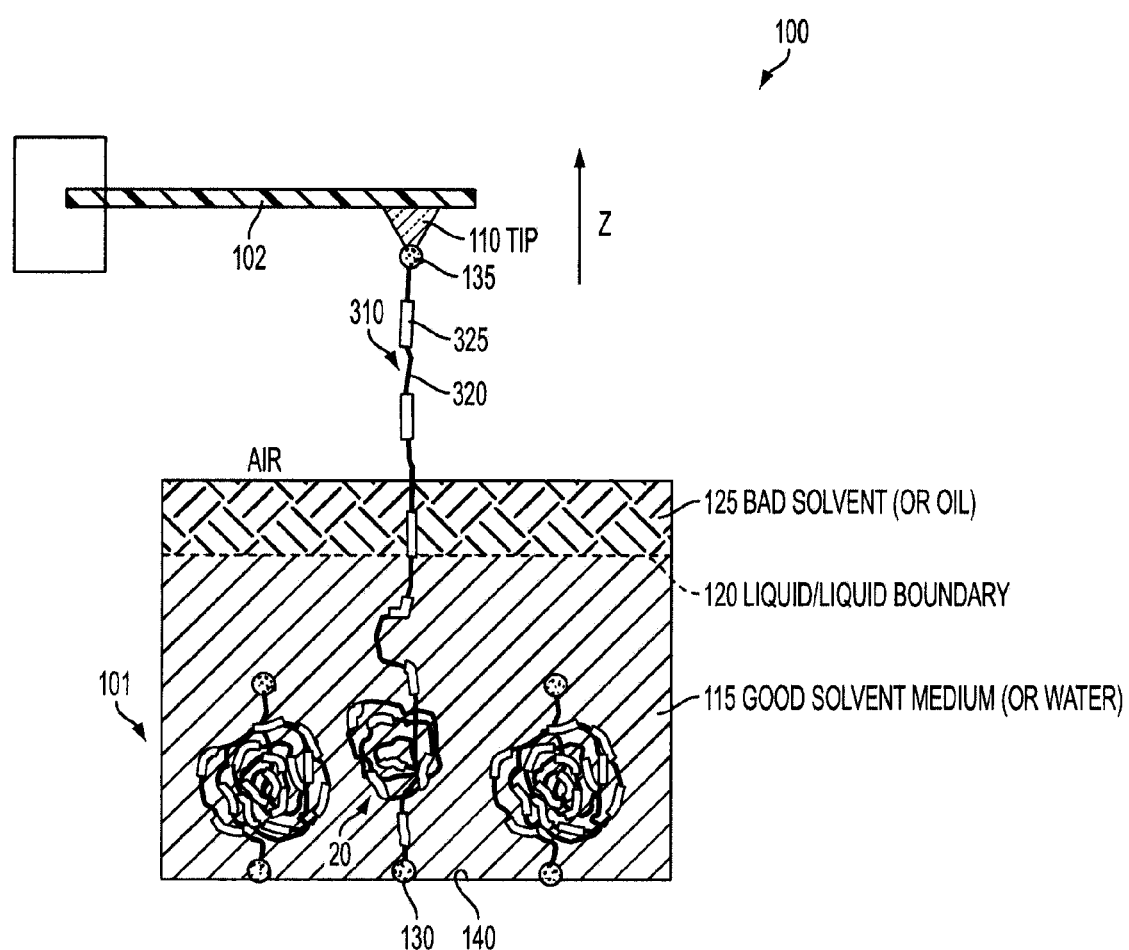
FIG. 3A illustrates the example setup for measuring the solvophobic force and energy of a diblock polymer strand and its nanoscale composition according to a second embodiment.

According to a second embodiment, FIG. 3A illustrates the example setup 100 for measuring the solvophobic force and energy of a diblock polymer strand 310 and its nanoscale composition. The nanoscale composition of the diblock polymer strand 310 is the length distributions of the two (repeating) blocks 320 and 325 of the polymer that make up the strand. This is equivalent to determining the "polydispersity" of the diblock copolymer strand 310 at the nanoscale with a precision determined by the AFM measurement setup that can reach about 0.1 nm. However, note that the polydispersity of a copolymer as determined by techniques like dynamic light scattering do not obtain the information about positional occurrence of the two blocks in either along a single strand, or in the bulk of the polymer. Polydispersity of a copolymer only provides the distribution of the hydrodynamic radius of the coil-like conformations taken up by the polymer strands in a solution and the associated polydispersity index. One end of the diblock polymer molecule 310 is bound to the bottom surface 140 of the chamber 101 and the other end to the tip 110 of the atomic force microscope 102. Pulling (at a constant rate) the AFM tip 110 (upward in the Z direction) unwinds and stretches the diblock polymer molecule 310 as the tip 110 applies a force on the molecule 310, all while the whole diblock polymer molecule 320 is still in the good solvent medium 115 (e.g., water). This force required to expose the segments (e.g., the block 320 and/or block 325) of the diblock polymer molecule 310 to the good solvent medium 115 results in a plateau (Plateau-I in FIG. 3B).

Figure 3B:
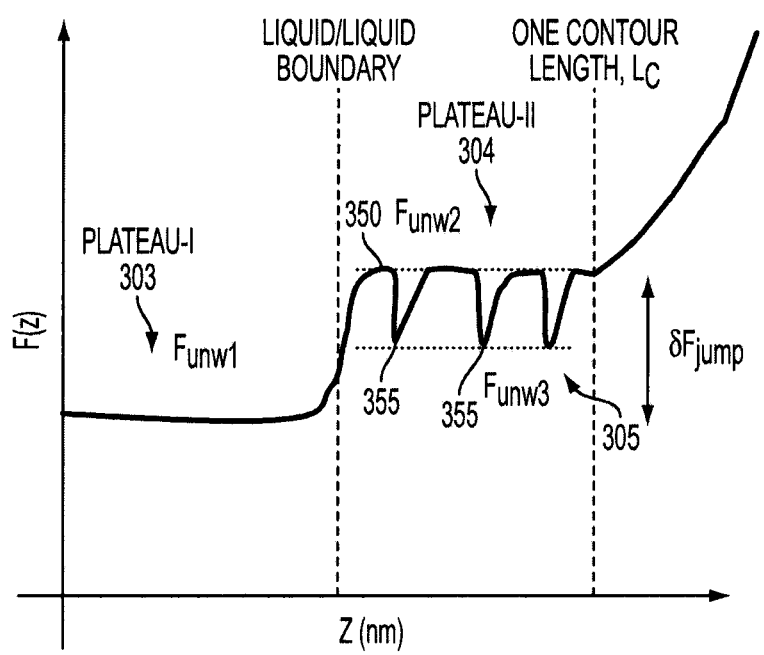
FIG. 3B illustrates a graph of the measured force versus molecular extension (F-x) curve according to the second embodiment.

FIG. 3B illustrates a graph of the measured force versus molecular extension (F-x) curve according to the second embodiment. While unwinding the molecule 310 from its random coil conformation 20 (i.e., a ball) in the good solvent medium 115 by pulling the AFM tip 110 upward in the Z direction, the force (designated as force unwind 1 or Funw1) applied by the AFM tip 110 reaches the first plateau designated as Plateau-I for the section 303 of the curve.

Figure 3C:
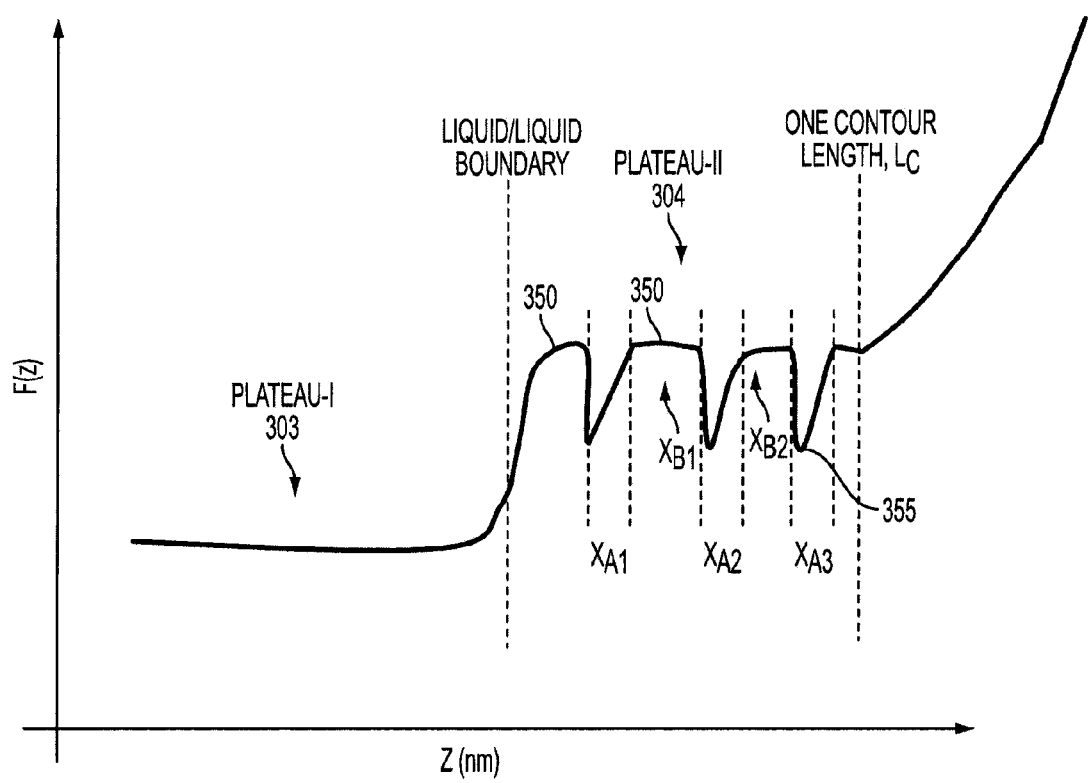
FIG. 3C illustrates the second plateau region in more detail according to the second embodiment.

Further pulling (at a constant rate) of the AFM tip 110 (upward in the Z direction away from the chamber 101) move one segment (e.g., block 320) of the two blocks 320 and 325 that repeat to make up the diblock polymer strand 310 to cross the good solvent medium to bad solvent medium boundary 120 resulting in the second plateau designated as Plateau-II is section 304 in the F-x curve. Pulling tip 110 (upward in the Z direction) even further will make a segment of the other block 325 of the diblock polymer strand 310 to cross the liquid to liquid boundary 120. Because the two blocks 320 and 325 have, in general, different energies of interaction with the solvent molecules of the good solvent medium 115 and bad solvent medium 125, this results in (either) an additional drop 355 and/or increase 350 in the force measured by the AFM tip 110 in the second plateau region (Plateau-II in section 304). The force-extension curve for the second plateau region therefore appears like a saw-tooth shape 305. This second plateau region (Plateau-II) is shown in more detail in FIG. 3C. From the positions (identified as XA1, XB1, XA2, XB2 and so on as the molecule 310 is pulled further) obtained from this section 304 of the curve, the nanoscale composition of the diblock copolymer 310 can be obtained. By analogy, this same method can also be applied to a tri-block and multi-block copolymer to obtain its nanoscale composition according to the features discussed herein. FIGS. 3A, 3B, and 3C may generally be referred to as FIG. 3.

Figure 4A:
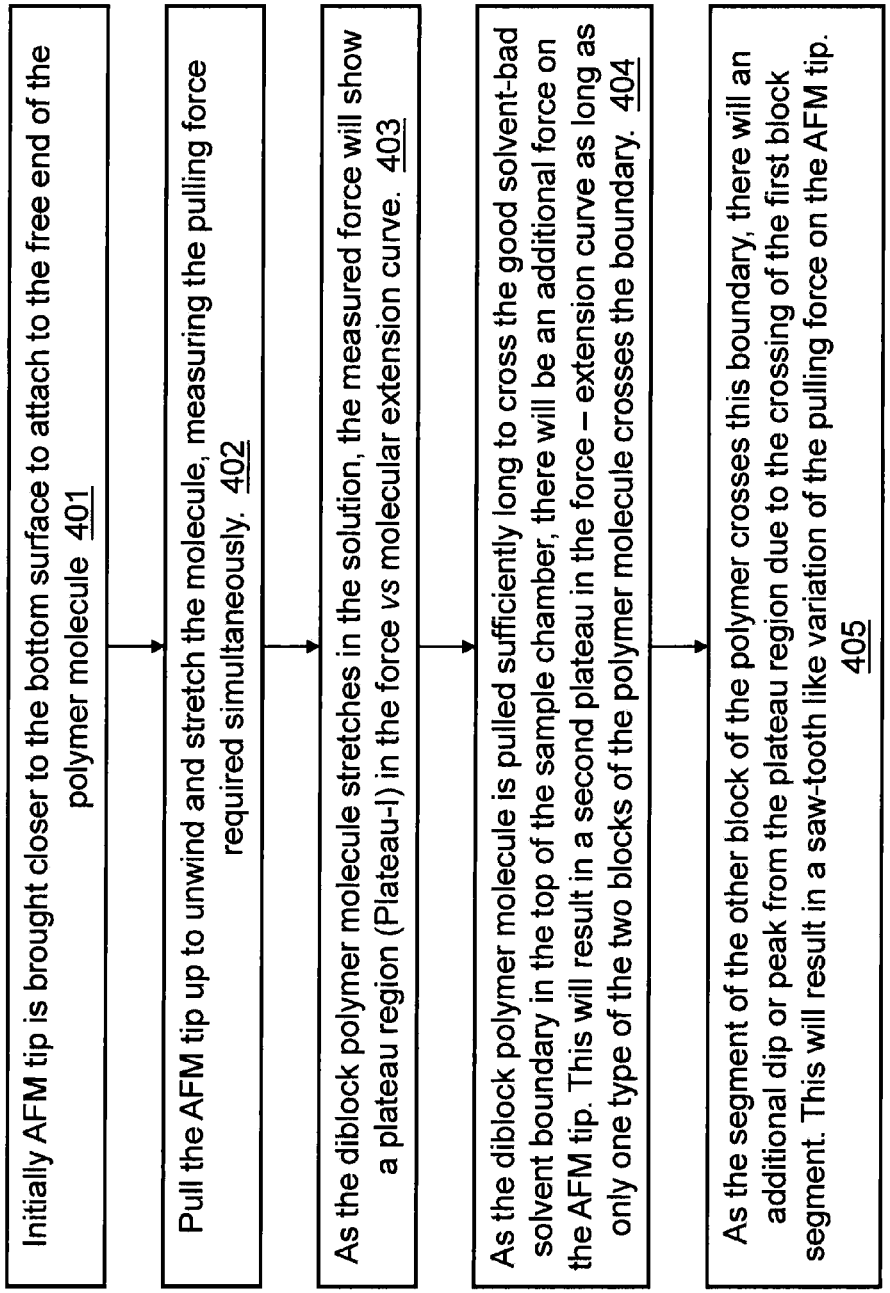

According to the second embodiment, FIGS. 4A and 4B together illustrate a method 400 for measuring the solvophobic energy and force of the diblock copolymer molecule 310 in the bad solvent medium 125 with respect to the good solvent medium 115 illustrated in FIG. 3. The polymer molecule 310 is functionalized with special chemical groups to attach 130 selectively to the bottom surface 140 of the sample chamber 101 and to attach 135 to the AFM tip 110. Note that in AFM force spectroscopy studies of elastin-like polypeptides, self-assembled monolayers of alkanethiols terminated with oligoethylene glycol were used to graft one end of the polypeptide strands through amine coupling. Amine coupling of the ethylene glycol was carried out by reacting the COOH groups for 30 minutes with 1-ethyl-3-(dimethylamino) propyl carbodiimide (EDAC) (0.4 M, Aldrich) and N-hydroxysuccinimide (NHS) (0.1 M, Aldrich) in Milli-Q™grade water. One end of the diblock copolymer strand could also be held by the bottom surface 140 by adsorption and the other end to the AFM tip 110 by adsorption as well.

Initially, the AFM tip 110 is brought close (e.g., manually or automatically) to the bottom surface 140 to attach 135 to the free end of the diblock polymer molecule 310 that will selectively bind to the AFM tip at block 401. For example, a chemical is pre-applied to the AFM tip 110, and the same chemical is configured to attach to a block (e.g., block 320 and/or block 325) of the diblock polymer molecule 310. The chemical has functionalization properties to both hold/attach to the tip 110 (once applied) and likewise attach to the block 320, 325 of the diblock polymer molecule 310 (at the free end not attached to bottom surface 140).

The AFM tip 110 is pulled (upward in the Z direction) to unwind and stretch the diblock polymer molecule 310, and the AFM 102 measures the force required at block 402. The AFM tip 110 stretches the diblock polymer molecule 310 further in the good solvent medium 115 such that the measured force exhibits a plateau region of Plateau-I in the force-extension curve (of FIG. 3) at block 403. Pulling the diblock polymer (strand) molecule 310 further make the first segment of the two blocks (such as, e.g., block 320 which is directly attached 135 to the AFM tip 110) (of the diblock copolymer molecule 310) cross the good solvent to bad solvent boundary 120 (i.e., the liquid to liquid boundary 120) near the top of the sample chamber 101; this results in a second plateau (Plateau-II) in the force-extension curve of FIG. 3B at block 404. The difference between the average force in the first and second plateau regions gives the solvophobic force of one segment of the diblock copolymer from which the solvation energy can be deduced. This is the difference between Funw1 in Plateau-I and Funw2 in Plateau-II.

Pulling the AFM tip 110 upward (in the Z direction) even further makes a segment of the other block (e.g., block 325) of the diblock polymer (strand) molecule 310 to cross the boundary 120 that results in additional valleys or peaks from the plateau region (Plateau-II). The peaks and valleys of the measured force appear as the saw-tooth like variation (as shown in FIG. 3C) of the pulling force on the AFM tip 110 at block 405. The nanoscale composition of the diblock copolymer molecule 310 can be obtained from this saw-tooth shaped force-extension curve at block 406. By making many measurements (via the AFM 102) with different strands of the copolymer, average nanoscale composition can be obtained for the polymer sample (diblock polymer molecule 310).

Figure 5A:
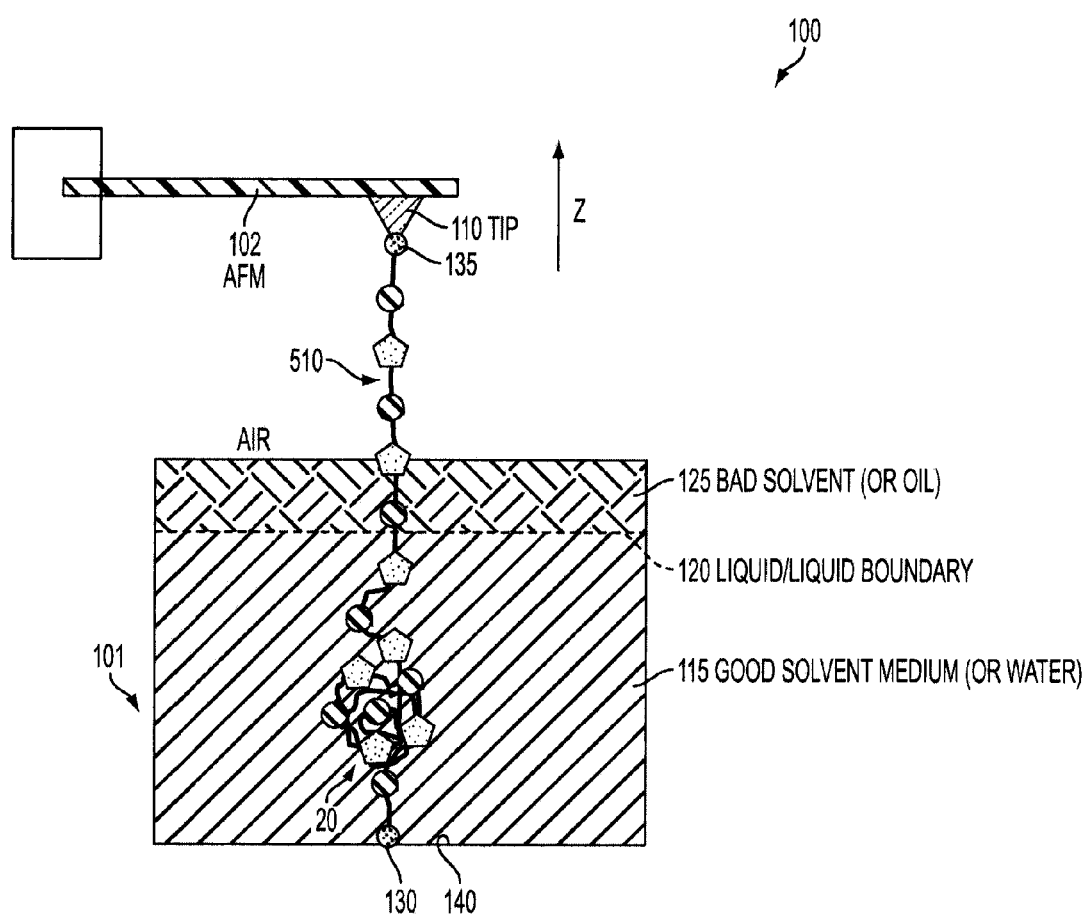
FIG. 5A illustrates an example setup for measuring the hydration and solvophobic force of a biomolecule according to a third embodiment.

FIG. 5A illustrates an example setup 100 for measuring the hydration and solvophobic force of a biomolecule 510 like a DNA molecule, RNA molecule, and/or protein molecule according to a third embodiment. For example purposes, the biomolecule is illustrated as the DNA molecule 510.

One end of the DNA molecule 510 is bound/attached 130 to the bottom surface 140 of the chamber 101 and the other end of the DNA molecule 510 is attached 135 to the tip 110 of the atomic force microscope 102. The DNA (or RNA) molecule 510 can be either single-stranded or double-stranded. Pulling (at a constant rate) the AFM tip 110 (upward in the Z direction) unwinds (from the ball 20) and stretches the DNA molecule 510 as the tip 110 applies a force on the DNA molecule 510, while the whole DNA molecule 510 remains in the good solvent medium 115. This force required to expose the segments (i.e., individual bases shown as shapes on the DNA molecule 510) of the DNA molecule 510 to the good solvent medium 115 as the DNA molecule 510 unwinds from its random coil conformation 20 results in a plateau (Plateau-I on section 503 in FIG. 5B).

Figure 5B:
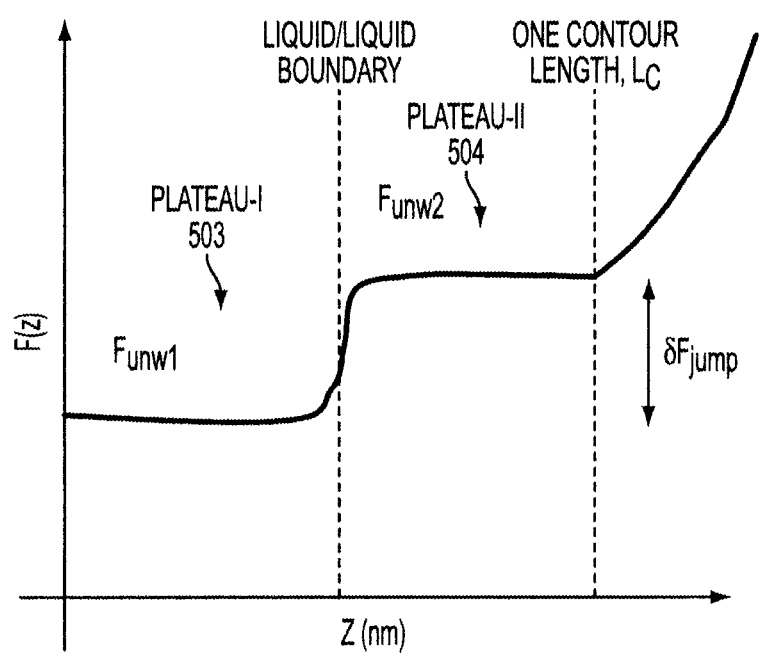
FIG. 5B illustrates a graph of the measured force versus molecular extension (F-x) curve according to the third embodiment.

FIG. 5B illustrates a graph of the measured force versus molecular extension (F-x) curve according to the third embodiment. While unwinding the DNA molecule 510 from its random coil conformation 20 (i.e., a ball) in the good solvent medium 115 by pulling the AFM tip 110 upward in the Z direction, the force (designated as force unwind 1 or Funw1) applied by the AFM tip 110 reaches the first plateau designated as Plateau-I for the section 503 of the curve.

Further pulling (at a constant rate) of the AFM tip 110 moves part of the DNA molecule 510 to cross the good solvent to bad solvent boundary 120 resulting in the second plateau (Plateau-II at section 504) in the F-x curve (as Funw2). The difference between the average force in the two plateau regions, δF=Funw1−Funw2, is the solvophobic force required to move the DNA or RNA segment (i.e., particular base) from the good solvent medium 115 to the bad solvent medium 125. This difference/change in force is directly related to the solvophobic energy of the DNA (or RNA) molecule 510 in the bad solvent medium 125 with respect to the good solvent medium 115. The AFM tip 110 (moving upward in the Z direction) pulls the DNA molecule 510 even further so that the extended molecular length is almost equal to its contour length Lc, the force (on the AFM tip 110) exhibits strong non-linear behavior which is related to the elastic property of the DNA molecule 510 influenced by its chemical nature. As noted earlier, Lc is the number of monomers x (i.e., bases) for the average separation between the monomers when the DNA molecule 510 in stretched conformation.

FIG. 6 illustrates a method 600 for measuring the hydration and solvophobic force of the biomolecule 510 (e.g., DNA, RNA, or protein). As noted above, the DNA molecule, RNA molecule, or protein molecule is suitably modified at both ends so that one end of the biomolecule 510 attaches 130 to the bottom surface 140 of the chamber 101 and the other end attaches 135 to the AFM tip 110. The operator brings the AFM tip 110 close to the bottom surface 140 so as to attach 135 the tip 110 to the free end of the biomolecule 510, all while the other end of the biomolecule 510 remains attached 130 to the bottom surface 140 at block 601. The operator pulls (at a constant rate) the AFM tip 110 (upward in the Z direction) to unwind the biomolecule 510 while measuring the force required at block 602. Stretching the molecule further in the good solvent medium results in a plateau in the force vs. molecular extension curve (shown as Plateau-I in section 503).

Pulling the biomolecule 510 even further (upward in the Z direction) results in the part (e.g., base) of the biomolecule 510 attached to the AFM tip 110 crossing the bad solvent medium 125 region, which results in the measured force appearing as the second plateau (Plateau-II in section 504) in the F-x curve at block 604. At block 605, the difference between the average force in the two plateau regions gives the solvophobic force required to move to the bad solvent medium 125 from the good solvent medium 115.

Figure 7A:
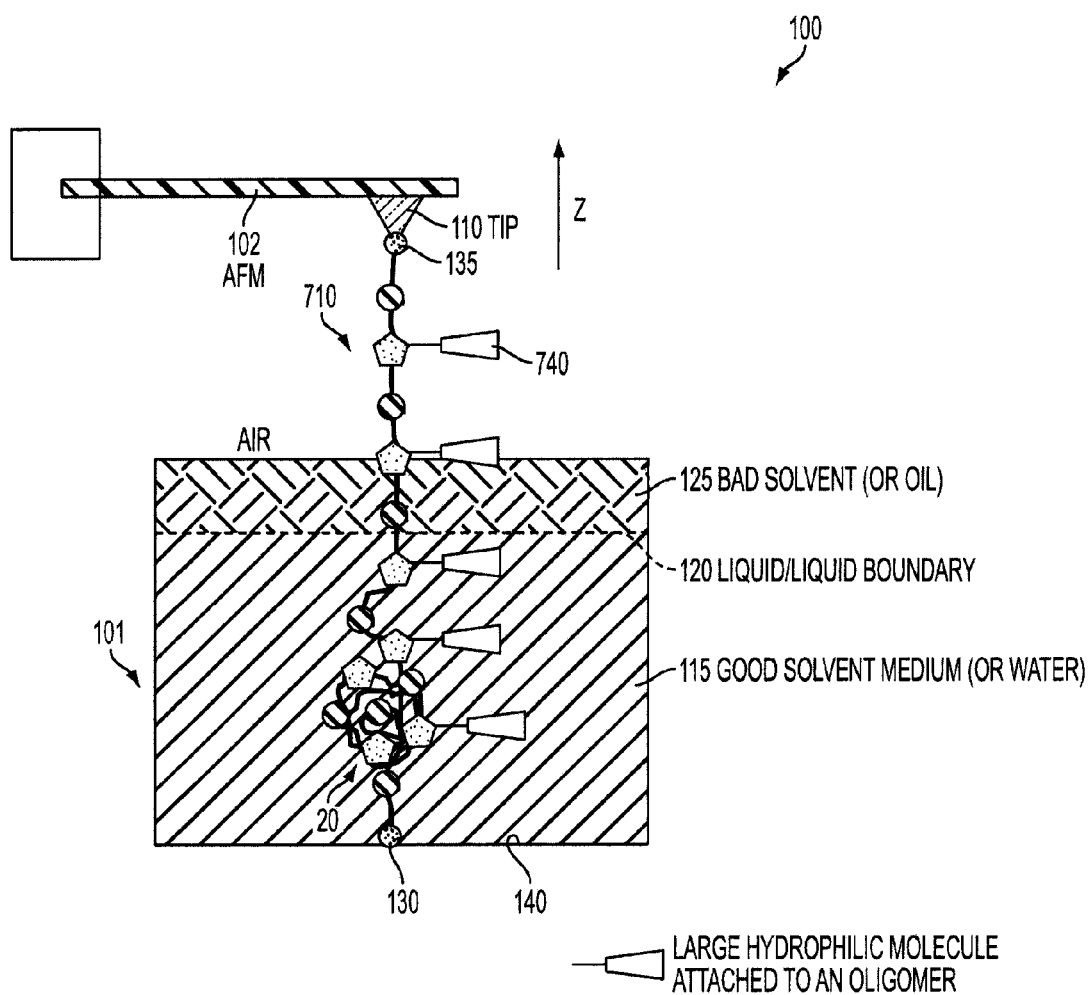
FIG. 7A illustrates an example setup for measuring the hydration and solvophobic force of the biomolecule with selected bases attached to large hydrophilic molecules according to a fourth embodiment.

According to a fourth embodiment, FIG. 7A illustrates an example setup 100 for measuring the hydration and solvophobic force of the biomolecule 710, such as, e.g., a DNA molecule or RNA molecule attached with large hydrophilic molecules 740 740 through a short oligomer of DNA or RNA. The oligomer binds to the complementary sequence in the DNA or RNA molecule. The oligomer can consist of 6 to 20 bases of DNA attached with the large hydrophilic molecule and it would bind to wherever its complementary sequence occurs in the long DNA or RNA molecule to be sequenced. An example for the biomolecule DNA is the single-stranded viral DNA M13mp18 (SEQ ID NO. 1). It is 7249 bases long and its contour length is about 5 μm in its fully stretched form. The sequence AATTCCTT occurs at three places separated by about 480 nm and 2.15 μm corresponding to 686 and 3066 bases. The complementary oligomers TTAAGGAA attached with biotin molecule at one end (can be obtained commercially from Midland Certified Co., Texas) would bind to the streptavidin coated polystyrene bead which will act as a large hydrophilic molecule. The complementary oligomers would preferentially bind to the single-stranded DNA M13mp18 wherever the sequence AATTCCTT occurs along the DNA. The hydrophilic nature of polystyrene bead and the streptavidin coating would provide the force variation necessary to distinguish the location of the oligomer along the ssDNA molecule (which then results in distinguishing the sequences of bases A, T, G, C or U). Further, regarding modification of the DNA or RNA molecule with the large hydrophilic molecule 740 is discussed below. For example purposes, the biomolecule 710 may be referred to as the DNA molecule 710.

The large hydrophilic molecule 740 attached to the selected segments of the DNA molecule 710 through short oligomers produces peaks in the measured force in Plateau-II (unlike the DNA molecule 510 (in FIG. 5) without the large hydrophilic molecules 740). A hydrophile is a molecule or other molecular entity that is attracted to and tends to be easily dissolved by water (as would be understood by one of ordinary skill in the art). An example of the large hydrophilic molecule 740 that may be chemically attached to segments (of the bases) of the DNA molecule 710 is polystyrene bead coated with protein molecules Steptavidin. (Commercially available, for example, from Bangs Laboratories Inc, Fishers, Ind. and Invitrogen (Life Technologies), Grand Island, N.Y.). The beads from these sources are available in varying sizes from 30 nm and above. As the large hydrophilic molecule 740 crosses the liquid-liquid boundary, there will be an increase in the measured force 750 by the AFM tip 110. Because the position at which these increases occur is also measured with a precision of 0.1 nm, this provides the exact positions of the oligomers along the DNA or RNA molecule (correspondingly the position of complementary sequences of bases of the DNA or RNA molecule). As a DNA (or RNA) sequencing method, information about the position or location of these modified groups (i.e., oligomers attached to the large hydrophilic molecule 740) along the DNA molecule 710 can also be obtained based on the respective measured forces identifying and corresponding to different sequences of oligomers of the same length attached to the large molecule 740. When this is done for a library of oligomers (for a word of length N, there are 4N possible oligomers corresponding to the four bases that each base in the oligomer can take), one can obtain the information about the occurrence of all these words along the DNA molecule for which the sequence information needs to be determined. Therefore, the sequence information about a DNA or RNA molecule can be obtained in this manner. For example, there are oligomers that have various sequences of the bases G, A, T, and C for DNA (where U replaces T for RNA) in the library so that each of the one oligomer is able to complementary attach to a segment of bases on the DNA molecule 710 be sequenced.

As understood by one skilled in the art complementarity is a property shared between two nucleic acid sequences, such that when they are aligned antiparallel to each other, the nucleotide bases at each position will be complementary. Two bases are complementary if they form Watson-Crick base pairs. For DNA, adenine (A) bases complement thymine (T) bases and vice versa; guanine (G) bases complement cytosine (C) bases and vice versa. With RNA, it is the same except that uracil is present in place of thymine, and therefore adenine (A) bases complement uracil (U) bases. Since there is only one complementary base for each of the bases found in DNA and in RNA, one can reconstruct a complementary strand for any single strand.

Now, returning to the example in FIG. 7A, one end of the DNA molecule 710 is bound/attached 130 to the bottom surface 140 of the chamber 101 and the other end is bound/attached 135 to the AFM tip 110 of the atomic force microscope 102. The modified DNA (or RNA) molecule 710 can be either single-stranded or double-stranded.

The operator-controlled software pulls the AFM tip 110 upward (in the Z direction at a constant rate), and this unwinds and stretches the DNA molecule 710 as the AFM tip 110 applies a measured force on the DNA molecule 710 (all while the whole DNA molecule 710 is still in the good solvent medium 115). This force, required to expose the segments (i.e., bases with and without the attached large molecule 740) of the DNA molecule 710 to the good solvent medium 115 as the DNA molecule 710 unwinds from its random coil conformation 20, results in a plateau (Plateau-I) in the force vs. molecular extension (F-x) curve shown in FIG. 7B.

Figure 7B:
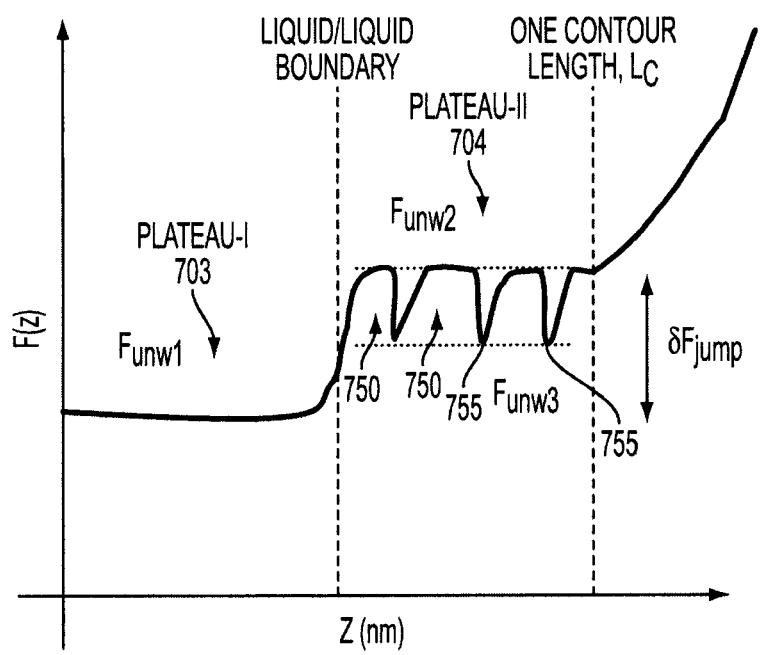
FIG. 7B illustrates a graph of the measured force versus molecular extension (F-x) curve according to the fourth embodiment.

FIG. 7B illustrates a graph of the measured force versus molecular extension (F-x) curve according to the fourth embodiment. While unwinding the DNA molecule 710 from its random coil conformation 20 (i.e., a ball) in the good solvent medium 115 by pulling the AFM tip 110 upward in the Z direction, the measured force (designated as force unwind 1 or Funw1) applied by the AFM tip 110 reaches the first plateau designated as Plateau-I for the section 703 of the curve.

Further pulling of the AFM tip 110 moves part of the DNA molecule 710 to cross the good solvent medium to bad solvent medium boundary 120 resulting in the second plateau (Plateau-II of section 704) in the F-x curve. Due to the presence of the large hydrophilic molecules 740 attached to select oligomers, there are additional jumps in the measured force plateau 704 resulting in saw-tooth like shape of the force-extension curve in this regime (each time the oligomer crosses the good solvent medium to bad solvent medium boundary 120). As explained for the case of determining the nanoscale composition of a diblock copolymer in FIG. 3, the position (on the DNA molecule 710) of the modified oligomers (i.e., respectively attached to the large hydrophilic molecule 740) can be obtained from the peak positions (the various peak 750 measured forces) in the saw-tooth shape of the force-extension curve in Plateau II shown in FIG. 7B. The repeated peak measured force (peaks 750) in the saw-tooth shape (of Plateau II) provides the position of the modified oligomers (respectively attached to the large hydrophilic molecule 740 on the DNA molecule 710) along with unmodified ones (i.e., DNA bases not attached to the large hydrophilic molecules 740 with valley 750 measured forces) is equivalent to sequencing the DNA or RNA molecule. The sequence information can be used to obtain different types of genetic information about an individual.

FIG. 8 illustrates a method 800 to obtain the position of the modified DNA segments/sequences of bases (i.e., each sequence or segment is a group of bases) attached to (complementary) oligomers (which are attached to the large hydrophilic molecule 740) along the DNA molecule 710 according to the fourth embodiment. Although the oligomers are not shown in FIG. 7A, the oligomer acts as the glue that allows large hydrophilic molecule 740 attach to the segment of bases. Therefore, each large hydrophilic molecule 740 is attached at each segment of bases (and there may be multiple segments along the DNA molecule 710). Each one of these segments (of bases) can be identified via the measured force of the large hydrophilic molecule 740. Since the bases of the oligomer are known in advance, the segment of the bases on the DNA molecule 710 are identified as the complement to the know bases of the oligomer.

The DNA molecule 710 (or RNA) with the large hydrophilic molecule 740 attached to an oligomer is in the sample chamber 101. Initially, one end is attached 130 to the bottom surface 140 of the sample chamber 101 and the AFM tip 110 is brought closer to the free end (the other end) to attach 135 to the free end of the DNA molecule 710 at block 801.

Pulling (at a constant rate) the AFM tip 110 (upward in the Z direction) unwinds and stretches the DNA molecule 710 while simultaneously measuring the pulling force at block 802, producing Plateau-I (section 703) in the force versus extension curve at block 803. As the modified DNA molecule 710 (or RNA) crosses the good solvent medium to bad solvent medium boundary 120, the additional (measured) force acting on the AFM tip 110 results in the second plateau (Plateau II in section 704) in the force at block 804. When the hydrophilic group attached to one type of base crosses this liquid to liquid boundary 120, there is an additional peak 750 in the plateau II region. This will results in a saw-tooth like variation of the pulling force on the AFM tip at block 805. The width of the dips/valleys 755 and/or peaks 750 in the saw-tooth structure provides the positional separation between the modified base along the DNA or RNA molecule at block 806.

FIG. 9 is a method 1000 of sequencing a block copolymer (e.g., diblock polymer strand 310).

The block copolymer (e.g., diblock polymer strand 310) is traversed (via pulling the AFM tip 110 in upward in the z direction at a constant rate) from a first medium (e.g., good solvent medium 115) to a second medium (e.g., bad solvent medium 125) at block 902. The block copolymer comprises first blocks (e.g., blocks 320) and second blocks (e.g., blocks 325).

The AFM 102 measures a first measured force (e.g., peak 350) when (each time) the first blocks traverse from the first medium to the second medium at block 904.

At block 906, the AFM 102 measures a second measured force (e.g., valley 355) when (each time) the second blocks traverse from the first medium to the second medium, where the first measured force (e.g., peak 350) is different from the second measured force (e.g., valley 355).

The first blocks of the block copolymer (diblock polymer strand 310) are identified based on measuring the first measured force (e.g., peaks 350) (each time) via the AFM 102 at block 908, and the second blocks of the block copolymer are identified based on measuring on the second measured force (e.g., valleys 355) at block 910.

In one case, the first measured force is a peak 350 when the first blocks respectively traverse from the first medium to the second medium, and the second measured force is a valley 355 when the second blocks respectively traverse from the first medium to the second medium.

The first medium (good solvent medium 115) is water. The second medium (bad solvent medium 125) is oil.

The block copolymer has a first end and a second end. The first end is attached 130 to a bottom surface 140 of a container 101, and the second end is attached 135 to a tip 110 of a measuring device (AFM 102) that measures forces.

The first measured force is a measured solvophobic force, and the second measured force is a different measured solvophobic force (of the same diblock polymer strand 310).

A length (e.g., lengths XB1, XB2, and so forth) of the first blocks and a location for each of the first blocks are determined based on each of the first blocks 325 respectively crossing the good solvent medium 115 to bad solvent medium 125 boundary 120. A length (e.g., lengths XA1, XA2, and so forth) of the second blocks and a location of each of the second blocks are determined based on each of the second blocks 320 respectively crossing the good solvent medium 115 to bad solvent medium 125 boundary 120. The first blocks and the second blocks are two types of monomer blocks.

The locations of the first blocks correspond to the times for the first measured force (e.g., the time for peak 350 repeats), and the locations of the second blocks correspond to the times for the second measured force (e.g., the time for the valley 355 repeats). The location of the first blocks and the second blocks respectively along the block copolymer is according to each occurrence of the first measured force and the second force in FIG. 3B.

The block copolymer may be a diblock copolymer, a triblock copolymer, and/or a multiblock copolymer.

Figure 10:
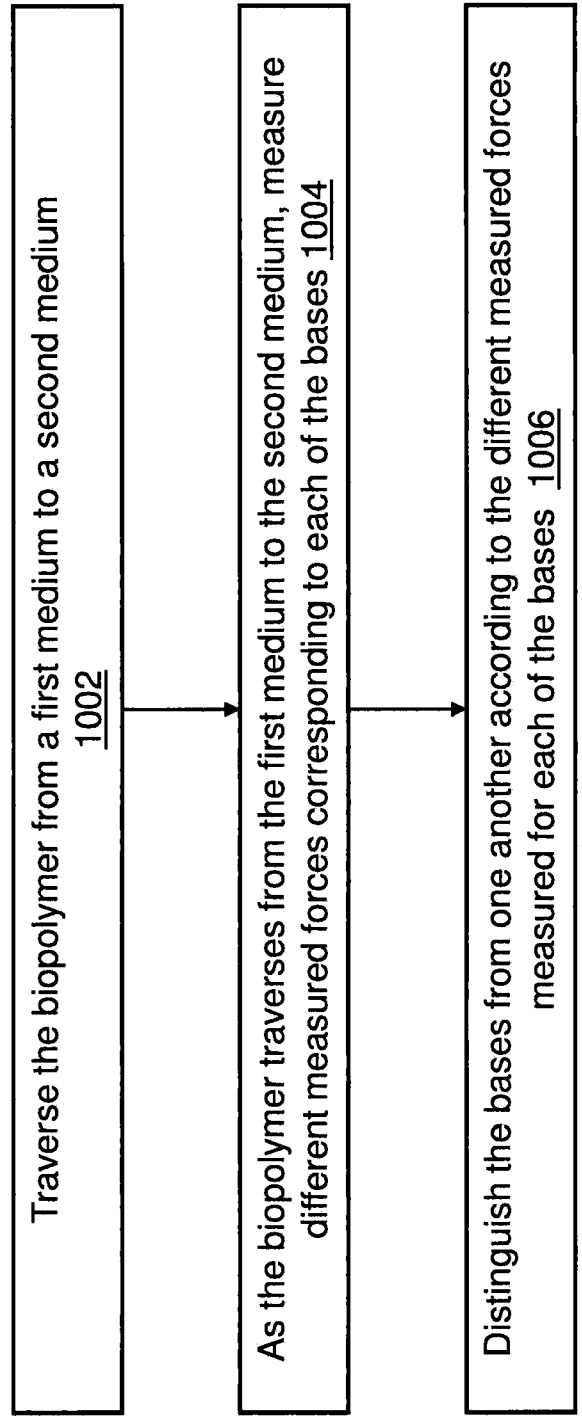
FIG. 10 is a method of sequencing a biopolymer/biomolecule according to an embodiment.

FIG. 10 is a method 1000 of sequencing a biopolymer (e.g., biopolymers 510 and 710).

The AFM 102 traverses (e.g., by pulling the AFM tip 110 in the z direction at a constant rate), the biopolymer (e.g., biopolymers 510 and 710) from a first medium (e.g., good solvent medium 115) to a second medium (e.g., bad solvent medium 125), where the biopolymer comprises bases at block 1002.

As the biopolymer traverses from the first medium to the second medium, the AFM 102 measures different measured forces (peaks and valleys) corresponding to each of the bases (and/or a group of bases) at block 1004.

Based on the different measurement via the AFM 102, the bases (and/or a group of the different bases) are distinguished from one another according to the different measured forces measured for each of the bases at block 1006.

Large molecules (e.g., such as different large molecules 740) are attached to selected ones of the bases (e.g., 1, 2, 3, and/or 4 bases) (and/or a group of the bases). The selected base is distinguished by a large measured force (e.g., valley 750). One or more different large molecules are respectively attached to the bases (and/or a group of bases via an oligomer).

Each of the different large molecules is chemically configured to attach to one type of the bases. The AFM tip 110 traverses the biomolecule from the first medium to the second medium with the different large molecules respectively attached to the different bases causes an increase (i.e., causes different valleys 750) in the different measured forces measured for each of the bases.

The biomolecule may be a DNA molecule, and/or an RNA molecule. The first medium (e.g., good solvent medium 115) is water, and the second medium (e.g., bad solvent medium 125) is oil.

More regarding the AFM 102 is discussed below. Atomic force microscopy (AFM) or scanning force microscopy (SFM) is a very high-resolution type of scanning probe microscopy, with demonstrated resolution on the order of fractions of a nanometer. The AFM is one of the foremost tools for imaging, measuring, and manipulating matter at the nanoscale. The information is gathered by "feeling" the surface with a mechanical probe. Piezoelectric elements that facilitate tiny but accurate and precise movements on (electronic) command enable the very precise scanning or movement of the AFM tip 110.

The AFM 102 consists of a cantilever with a sharp tip (probe) 110 at its end that is used to scan or touch the specimen surface. The cantilever is typically silicon or silicon nitride with a tip radius of curvature on the order of nanometers. When the tip 110 is brought into proximity of a sample surface (e.g., to touch), forces between the tip and the sample lead to a deflection of the cantilever according to Hooke's law. In embodiments, the AFM tip 110 is moved to touch or nearly touch the free end of the molecule being tested so that the AFM tip 110 attaches 135 (chemically and/or physically to the free end of the molecule as discussed herein.

Depending on the situation, forces that are measured in AFM include mechanical contact force, van der Waals forces, capillary forces, chemical bonding, electrostatic forces, magnetic forces, Casimir forces, solvation forces, etc. Along with force, additional quantities may simultaneously be measured through the use of specialized types of probes.

The AFM 102 include electronics (such as detectors, etc.) for measuring forces as discussed herein, and understood by one skilled in the art.

Figure 11:
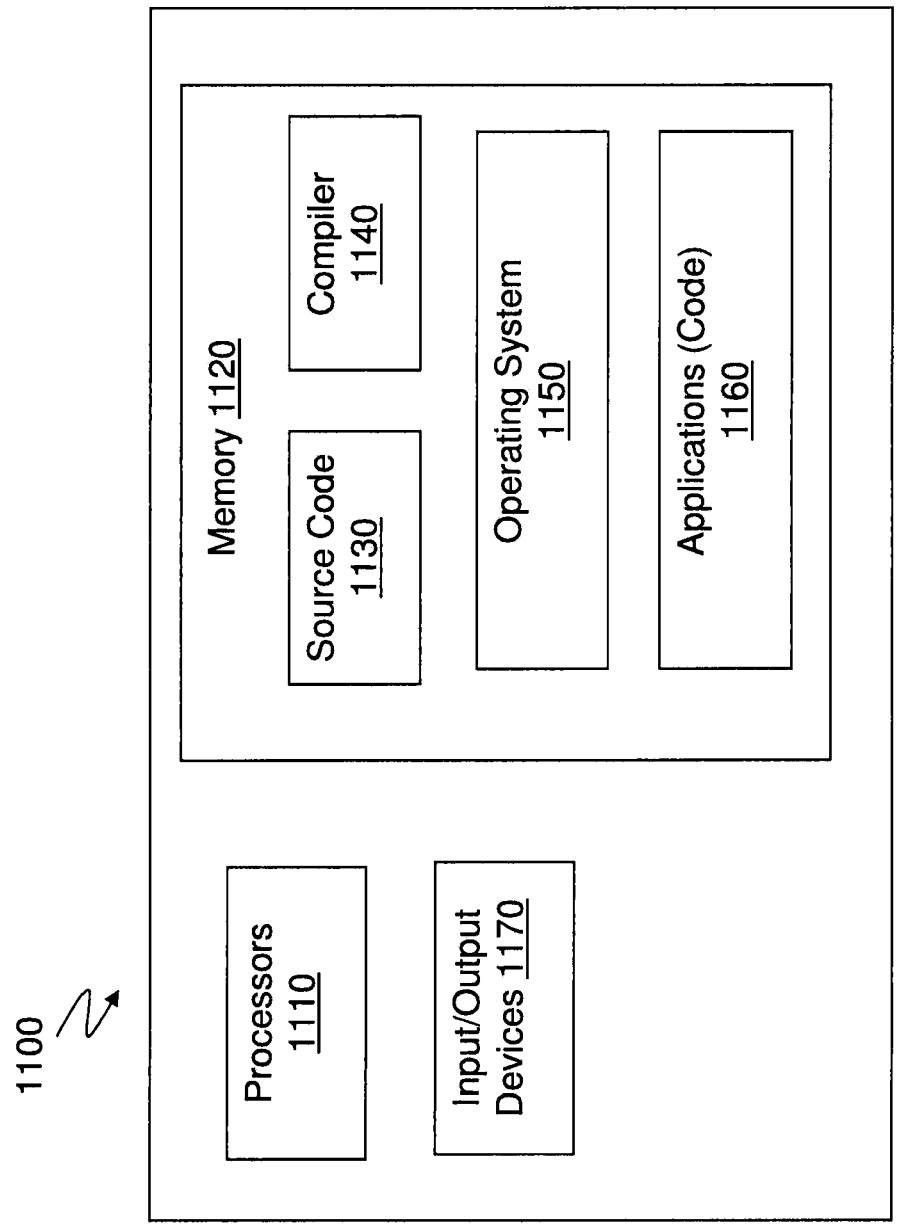
FIG. 11 is an example computer (computer setup) having capabilities, which may be included in and/or combined with embodiments.

Now turning to FIG. 11, an example illustrates a computer 1100 (e.g., any type of computer system connected to and/or implemented in the AFM 102) that may implement features discussed herein. The computer 1100 may be a distributed computer system over more than one computer. Various methods, procedures, modules, flow diagrams, tools, applications, circuits, elements, and techniques discussed herein may also incorporate and/or utilize the capabilities of the computer 1100. Indeed, capabilities of the computer 1100 may be utilized to implement features and/or be utilized in conjunction with exemplary embodiments discussed herein in FIGS. 1-10.

Generally, in terms of hardware architecture, the computer 1100 may include one or more processors 1110, computer readable storage memory 1120, and one or more input and/or output (I/O) devices 1170 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 1110 is a hardware device for executing software that can be stored in the memory 1120. The processor 1110 can be virtually any custom made or commercially available processor, a central processing unit (CPU), a data signal processor (DSP), or an auxiliary processor among several processors associated with the computer 1100, and the processor 1110 may be a semiconductor based microprocessor (in the form of a microchip) or a macroprocessor.

The computer readable memory 1120 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 1120 may incorporate electronic, magnetic, optical, and/or other types of storage media. Note that the memory 1120 can have a distributed architecture, where various components are situated remote from one another, but can be accessed by the processor(s) 1110.

The software in the computer readable memory 1120 may include one or more separate programs, each of which comprises an ordered listing of executable instructions for implementing logical functions. The software in the memory 1120 includes a suitable operating system (O/S) 1150, compiler 1140, source code 1130, and one or more applications 1160 of the exemplary embodiments. As illustrated, the application 1160 comprises numerous functional components for implementing the features, processes, methods, functions, and operations of the exemplary embodiments.

The operating system 1150 may control the execution of other computer programs, and provides scheduling, input-output control, file and data management, memory management, and communication control and related services.

The application 1160 may be a source program, executable program (object code), script, or any other entity comprising a set of instructions to be performed. When a source program, then the program is usually translated via a compiler (such as the compiler 1140), assembler, interpreter, or the like, which may or may not be included within the memory 1120, so as to operate properly in connection with the O/S 1150. Furthermore, the application 1160 can be written as (a) an object oriented programming language, which has classes of data and methods, or (b) a procedure programming language, which has routines, subroutines, and/or functions.

The I/O devices 1170 may include input devices (or peripherals) such as, for example but not limited to, a mouse, keyboard, scanner, microphone, camera, etc. Furthermore, the I/O devices 1170 may also include output devices (or peripherals), for example but not limited to, a printer, display, etc. Finally, the I/O devices 1170 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 1170 also include components for communicating over various networks, such as the Internet or an intranet. The I/O devices 1170 may be connected to and/or communicate with the processor 1110 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 1160 is implemented in hardware, the application 1160 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method of sequencing a polymer, comprising:
vertically traversing the polymer from a first medium to a second medium in a chamber, wherein a first end of the polymer is connected to an atomic force microscope and a second end of the polymer is connected to a bottom surface of the chamber;
wherein the polymer comprises blocks;
wherein the first medium is water and the second medium is oil;
as the polymer vertically traverses from the first medium to the second medium, measuring different measured forces corresponding to each of the blocks; and
distinguishing the blocks from one another according to the different measured forces measured for each of the blocks, the distinguishing comprises:
determining a plateau I and plateau II from the different measured forces, the plateau I defined to include a force for unwinding and stretching the polymer while in the first medium, the plateau II defined as crossing a boundary from the first medium to the second medium;
determining a solvophobic force of one block of the polymer by a difference in the plateau I and the plateau II.

2. The method of claim 1, further comprising attaching large molecules to selected ones of the blocks.

3. The method of claim 2, further comprising distinguishing the selected ones of the blocks by a large measured force.

4. The method of claim 1, further comprising attaching one or more different large molecules respectively to the blocks.

5. The method of claim 4, wherein each of the different large molecules are chemically configured to attach to one type of the blocks.

6. The method of claim 5, further comprising traversing the polymer from the first medium to the second medium with the different large molecules respectively attached to the blocks causes an increase in the different measured forces measured for each of the blocks.

7. The method of claim 1, wherein the polymer is a DNA molecule or an RNA molecule.

8. The method of claim 1, wherein the first medium fills a bottom portion of the chamber and the second medium fills an upper portion of the chamber, the first and second mediums being different.

9. The method of claim 1, wherein the plateau II is defined to include a saw-tooth shaped curve, wherein a composition of the polymer is determined from the saw-tooth shaped curve.

\* \* \* \* \*

SEQUENCE LISTING

```
<160> NUMBER OF SEQ ID NOS: 1

<210> SEQ ID NO 1
<211> LENGTH: 7249
<212> TYPE: DNA
<213> ORGANISM: Bacteriophage M13mp18

<400> SEQUENCE: 1
aatgctacta ctattagtag aattgatgcc acctttcag ctcgcgcccc aaatgaaaat      60
atagctaaac aggttattga ccatttgcga aatgtatcta atggtcaaac taaatctact    120
cgttcgcaga attgggaatc aactgttaca tggaatgaaa cttccagaca ccgtacttta    180
gttgcatatt taaacatgt tgagctacag caccagattc agcaattaag ctctaagcca    240
tccgcaaaaa tgacctctta tcaaaggag caattaaagg tactctctaa tcctgacctg     300
ttggagtttg cttccggtct ggttcgcttt gaagctcgaa ttaaaacgcg atatttgaag    360
tctttcgggc ttcctcttaa tcttttgat gcaatccgct ttgcttctga ctataatagt     420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600 ggttttatc gtcgtctggt aaacgagggt tatgatagtg ttgctcttac tatgcctcgt    660
```

```
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttc    900
tcgtcagggc aagccttatt cactgaatga gcagctttgt tacgttgatt tgggtaatga    960
atatccggtt cttgtcaaga ttactcttga tgaaggtcag ccagcctatg cgcctggtct   1020
gtacaccgtt catctgtcct cttttcaaagt tggtcagttc ggttccctta tgattgaccg   1080
tctgcgcctc gttccggcta agtaacatgg agcaggtcgc ggatttcgac acaatttatc   1140
aggcgatgat acaaatctcc gttgtacttt gtttcgcgct tggtataatc gctggggtc    1200 aaagatgagt gttttagtgt attctttcgc ctctttcgtt ttaggttggt gccttcgtag   1260
tggcattacg tattttaccc gtttaatgga aacttcctca tgaaaagtc tttagtcctc    1320 aaagcctctg tagccgttgc taccctcgtt ccgatgctgt cttttcgctgc tgagggtgac   1380 gatcccgcaa aagcggcctt taactccctg caagcctcag cgaccgaata tatcggttat   1440
gcgtgggcga tggttgttgt cattgtcggc gcaactatcg gtatcaagct gtttaagaaa   1500
ttcacctcga aagcaagctg ataaaccgat acaattaaag gctccttttg gagccttttt   1560
ttttggagat tttcaacgtg aaaaaattat tattcgcaat tcctttagtt gttccttttct  1620 attctcactc cgctgaaact gttgaaagtt gtttagcaaa accccataca gaaaattcat   1680
ttactaacgt ctggaaagac gacaaaactt tagatcgtta cgctaactat gagggttgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgg cggttctgag ggtggcggta ctaaacctcc tgagtacggt gatacaccta   1920
ttccgggcta tacttatatc aaccctctcg acggcactta tccgcctggt actgagcaaa   1980
accccgctaa tcctaatcct tctcttgagg agtctcagcc tcttaatact ttcatgtttc   2040
agaataatag gttccgaaat aggcagggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgaag   2220
atccattcgt ttgtgaatat caaggccaat cgtctgacct gcctcaacct cctgtcaatg   2280
ctggcggcgg ctctggtggt ggttctggtg gcggctctga gggtggtggc tctgagggtg   2340
gcggttctga gggtggcggc tctgaggag gcggttccgg tggtggctct ggttccggtg   2400
attttgatta tgaaaagatg gcaaacgcta ataaggggggc tatgaccgaa aatgccgatg   2460
aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
ttgtctttag cgctggtaaa ccatatgaat tttctattga ttgtgacaaa ataaacttat   2760
tccgtggtgt ctttgcgttt ctttttatatg ttgccacctt tatgtatgta ttttctacgt   2820
ttgctaacat actgcgtaat aaggagtctt aatcatgcca gttcttttgg gtattccgtt   2880
attattgcgt ttcctcggtt tccttctggt aactttgttc ggctatctgc ttacttttct   2940
taaaaagggc ttcggtaaga tagctattgc tatttcattg tttcttgctc ttattattgg   3000
gcttaactca attcttgtgg gttatctctc tgatattagc gctcaattac cctctgactt   3060
```

```
tgttcagggt gttcagttaa ttctcccgtc taatgcgctt ccctgttttt atgttattct    3120
ctctgtaaag gctgctattt tcatttttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt acttacctt     3660 ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc tttttctagt aattatgatt    3840
ccggtgttta ttcttatttta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg ctaataattt tgatatggtt ggttcaattc cttccataat tcagaagtat    4500
aatccaaaca atcaggatta tattgatgaa ttgccatcat ctgataatca ggaatatgat    4560
gataattccg ctccttctgg tggttttctt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgcaccta aagatatttt agataaccct cctcaattcc tttctactgt tgatttgcca    4800
actgaccaga tattgattga gggtttgata tttgaggttc agcaaggtga tgctttagat    4860
ttttcatttg ctgctggctc tcagcgtggc actgttgcag cgctgttaa tactgaccgc    4920 ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca aagggttctt atctctgttg gccagaatgt ccctttttatt   5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caagattctg gcgtaccgtt cctgtctaaa    5400
```

```
atcccttaa tcggcctcct gtttagctcc cgctctgatt ccaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gcccttgac     5760 gttggagtcc acgttcttta atagtggact cttgttccaa actggaacaa cactcaaccc    5820
tatctcgggc tattcttttg atttataagg gattttgccg atttcggaac caccatcaaa    5880 caggatttc gcctgctggg gcaaaccagc gtggaccgct tgctgcaact ctctcagggc    5940
caggcggtga agggcaatca gctgttgccc gtctcgctgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360 atccccctt cgccagctgg cgtaatagcg aagaggcccg caccgatcgc ccttcccaac    6420
agttgcgcag cctgaatggc gaatggcgct ttgcctggtt tccggcacca gaagcggtgc    6480
cggaaagctg gctggagtgc gatcttcctg aggccgatac ggtcgtcgtc ccctcaaact    6540
ggcagatgca cggttacgat gcgcccatct acaccaacgt aacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa cgcgaatttt aacaaaatat taacgtttac    6780
aatttaaata tttgcttata caatcttcct gttttggggg cttttctgat tatcaaccgg    6840
ggtacatatg attgacatgc tagttttacg attaccgttc atcgattctc ttgtttgctc    6900
cagactctca ggcaatgacc tgatagcctt tgtagatctc tcaaaatag ctaccctctc      6960 cggcattaat ttatcagcta gaacggttga atatcatatt gatggtgatt tgactgtctc    7020
cggcctttct caccctttg aatctttacc tacacattac tcaggcattg catttaaaat    7080
atatgagggt tctaaaaatt tttatccttg cgttgaaata aaggcttctc ccgcaaaagt    7140
attacagggt cataatgttt ttggtacaac cgatttagct ttatgctctg aggctttatt    7200 gcttaattt gctaattctt tgccttgcct gtatgattta ttggatgtt                 7249
```